US00PP35005P3

(12) United States Plant Patent
Bentley

(10) Patent No.: US PP35,005 P3
(45) Date of Patent: Feb. 28, 2023

(54) ***ANISODONTEA* PLANT NAMED 'IB710-1'**

(50) Latin Name: *Anisodontea capensis*
Varietal Denomination: IB710-1

(71) Applicant: Plant Growers Australia Pty, Ltd., Wonga Park (AU)

(72) Inventor: Howard Bentley, Wonga Park (AU)

(73) Assignee: Plant Growers Australia Pty. Ltd., Wonga Park (AU)

( * ) Notice: Subject to any disclaimer, the term of this patent is extended or adjusted under 35 U.S.C. 154(b) by 0 days.

(21) Appl. No.: 17/803,319

(22) Filed: May 9, 2022

(65) Prior Publication Data

US 2022/0361390 P1 Nov. 10, 2022

Related U.S. Application Data

(60) Provisional application No. 63/185,702, filed on May 7, 2021.

(51) Int. Cl.
*A01H 5/02* (2018.01)
*A01H 6/60* (2018.01)

(52) U.S. Cl.
USPC ..... Plt./263.1
CPC ..... *A01H 6/60* (2018.05)

(58) Field of Classification Search
USPC ..... Plt./263.1
CPC ..... A01H 6/60; A01H 5/02
See application file for complete search history.

*Primary Examiner* — Keith O. Robinson
(74) *Attorney, Agent, or Firm* — Samuel R. McCoy, Jr.

(57) ABSTRACT

A new and distinct *Anisodontea capensis* plant named 'IB710-1' which is characterized by a compact, densely foliaged growth, an abundance of large flowers, flowers with a dark red center which become progressively lighter towards the apex and margins of the flower petals, dark red floral veins, and the stability of these characteristics from generation to generation.

2 Drawing Sheets

Latin name of the genus and species: The Latin name of the genus and species of the novel variety disclosed herein is *Anisodontea capensis*.

Variety denomination: The inventive variety of *Anisodontea capensis* disclosed herein has been given the variety denomination 'IB710-1'.

BACKGROUND OF THE INVENTION

Parentage: 'IB710-1' is a seedling selection resulting from the controlled cross pollination of *Anisodontea capensis* 'Dryspell Raspberry' (not patented), the seed parent, with *Anisodontea capensis* 'El Royo' (not patented), the pollen parent. In the late summer of 2017 the above pollination occurred at the breeding site located in Wonga Park, Victoria, Australia. Seeds were collected from 'Dryspell Raspberry', sown, and seedlings were grown out to maturity, during the spring of 2017. One of the resulting plants was observed to exhibit medium to dense foliage, and shorter plant height, an abundance of large flowers, and red-purple flowers that fade to very light red-purple towards the outer region of the corolla. The seedling was isolated for further evaluation to confirm the distinctness and stability of the characteristics first observed. Upon confirmation of distinctness and stability, 'IB710-1' was selected for commercialization.

Asexual Reproduction: 'IB710-1' was first asexually reproduced by way of softwood stem cuttings in the spring of 2017 at the inventor's nursery in Wonga Park, Victoria, Australia. Through eight subsequent generations, the unique features of this cultivar have proven to be stable and true to type.

SUMMARY OF THE INVENTION

The following characteristics have been repeatedly observed and represent the distinguishing characteristics of the new *Anisodontea capensis* plant, 'IB710-1'. These traits, in combination, distinguish 'IB710-1' as a new and distinct cultivar.

1. 'IB710-1' exhibits a compact and densely-foliaged growth habit; and
2. 'IB710-1' exhibits an abundance of large flowers; and
3. 'IB710-1' exhibits pale red flower petals which are dark red at the base and become progressively lighter towards the apex and margins; and
4. 'IB710-1' exhibits flower petals which are veined dark red.

BOTANICAL DESCRIPTION OF THE PLANT

Figure 1:
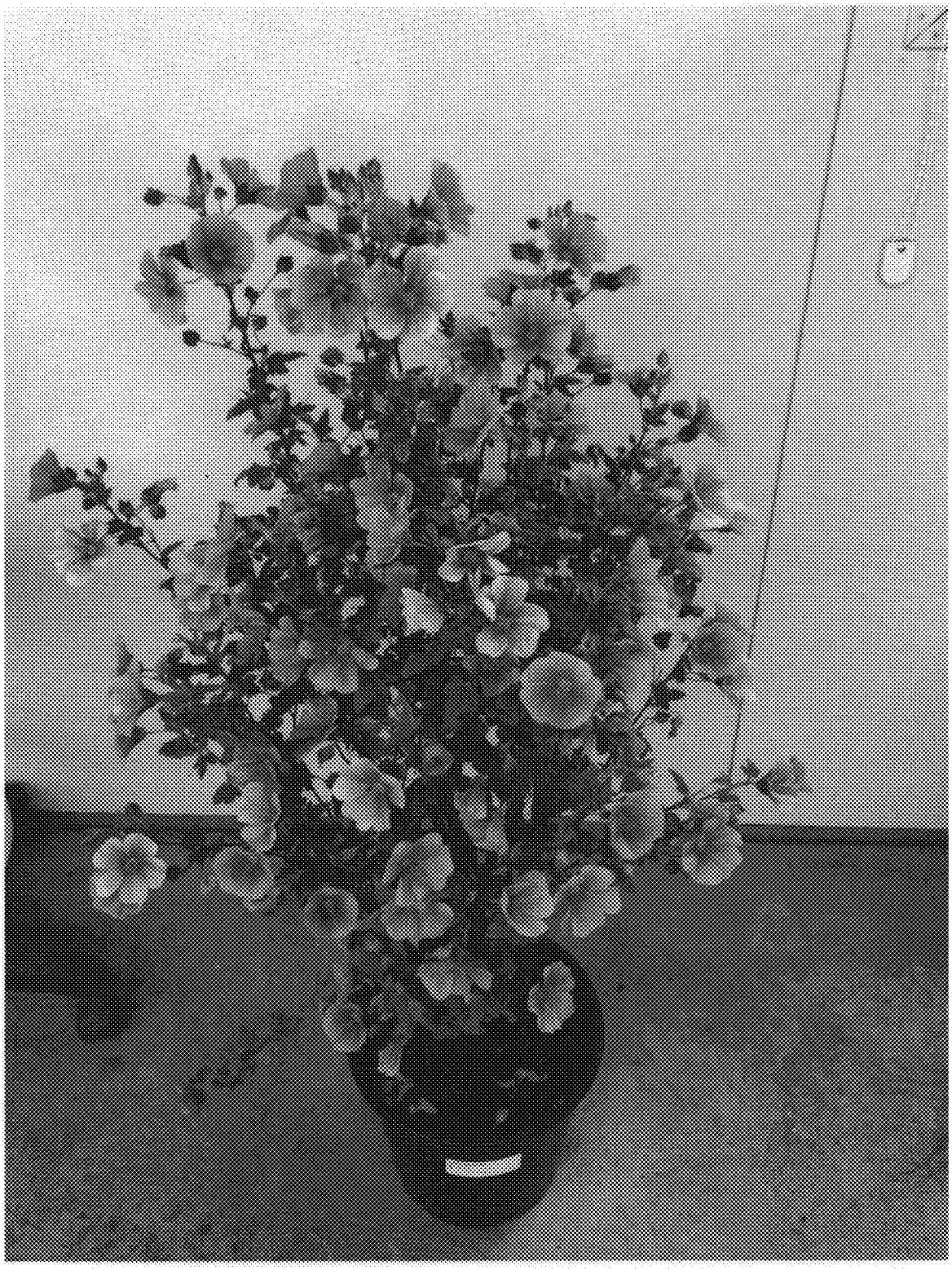
FIG. 1 illustrates, as nearly true as it is reasonably possible to make the same in color photographs of this type, an exemplary mature 'IB710-1' plant grown outdoors in Wonga Park, Victoria, Australia.
Figure 2:
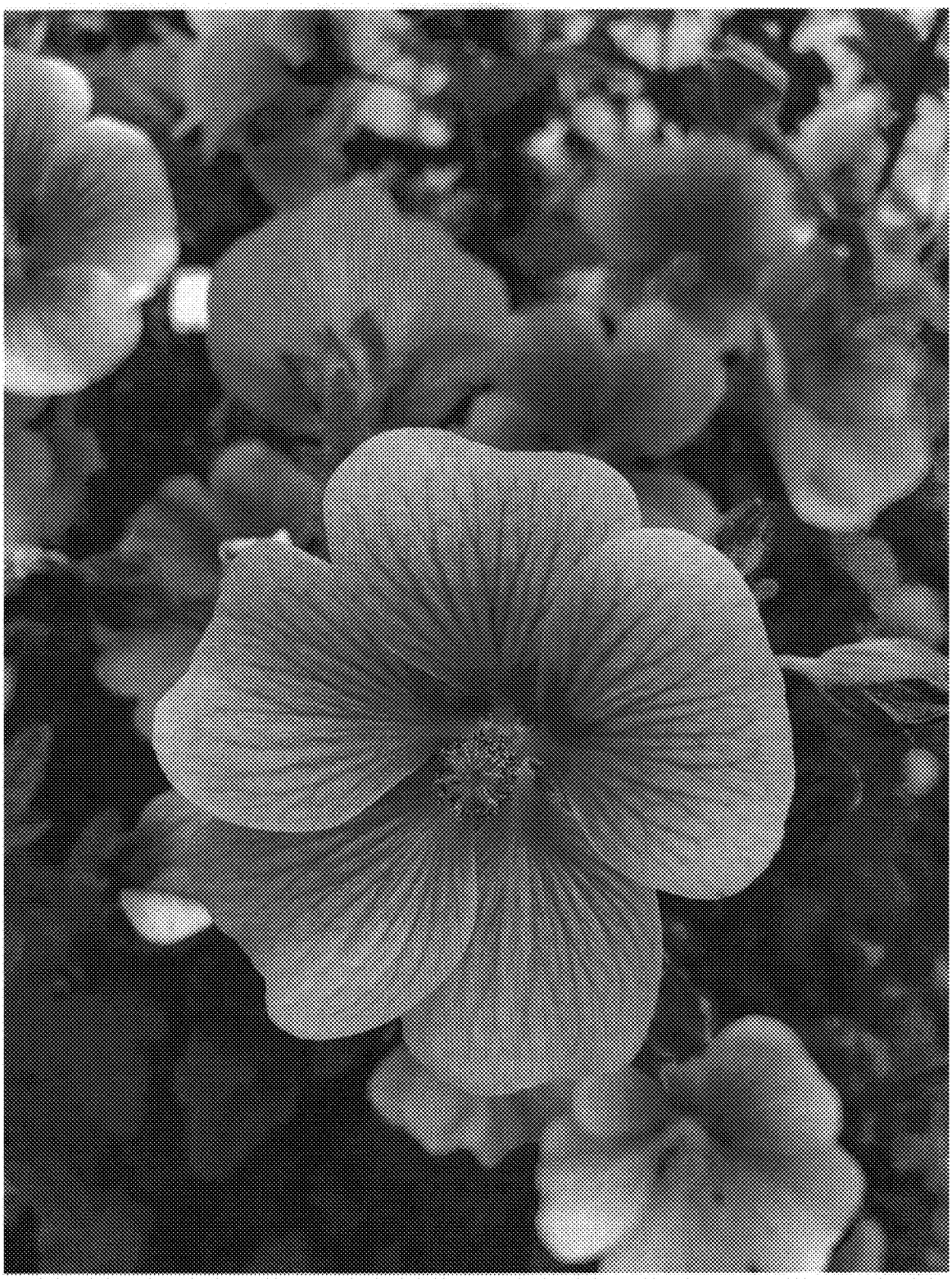
FIG. 2 illustrates, as nearly true as it is reasonably possible to make the same in color photographs of this type, exemplary flowers of a mature 'IB710-1' plant grown outdoors in Wonga Park, Victoria, Australia.

The following observations and measurements were made in August of 2022 and describe a 6-month-old 'IB710-1' plant grown outdoors in Greeleyville, S.C., in a 15 cm nursery container. The plant was allowed to grow with full sun exposure and maintained with regular overhead irrigation and slow-release granular fertilizer applications. Preventative disease and pest control measures were utilized in production.

Those skilled in the art will appreciate that certain characteristics will vary with older or, conversely, with younger plants. 'IB710-1' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 1986 (third edition).

A botanical description of 'IB710-1' and comparisons with the parents and most similar variety of common knowledge are provided below.

General plant description:

*Growth habit*.—Evergreen sub-shrub.
*Plant profile*.—Upright globular.
*Height*.—74.0 cm from the soil level to the top of the foliar plane.
*Plant spread*.—49.0 cm.
*Plant vigor*.—Moderately vigorous.
*Propagation type*.—Softwood stem cuttings.
*Time to produce a rooted cutting*.—Approximately 50 to 60 days to produce a rooted cutting at approximately 30 degrees Celsius.
*Time to produce a finished plant*.—24 weeks to produce a well-rooted 15 cm container.
*Disease resistance*.—Neither resistance nor susceptibility to typical *Anisodontea* pests and diseases has been observed.
*Environmental tolerances*.—Adapt to, at least, USDA Zones 9 through 11; moderate tolerance to rain; moderate tolerance to wind; drought tolerant once established.

Root system:

*General*.—Densely and freely branched rooting; roots are moderately fibrous.
*Distribution in the soil profile*.—Shallow to moderately deep.

Stem:

*General branching habit*.—Multiple main stems, freely branching from the base, with an abundance of lateral branches.
*Quantity of main stems per plant*.—6.
*Diameter of the main stem*.—0.9 cm at the base.
*Abundance of lateral branches*.—Abundant.
*Length of lateral branches*.—Approximately 42.0 cm.
*Diameter of lateral branches*.—Approximately 6.0 mm.
*Internode length*.—Ranging from 3.5 to 5.5 cm.
*Attitude of lateral branches*.—Upright and slightly outward.
*Aspect*.—Rounded.
*Texture, juvenile*.—Densely pubescent.
*Texture, mature*.—Moderately pubescent.
*Texture, oldest wood*.—Glabrous.
*Luster*.—Slightly glossy to matte.
*Strength*.—Strong.
*Color, juvenile lateral branches*.—Yellow-green, nearest to in between RHS 144A and 146D, and becoming progressively suffused with greyed-purple with age, RHS 183C.
*Color, mature lateral branches*.—Greyed-purple, nearest to RHS 1836.
*Color, oldest wood*.—Nearest to a mixture of greyed-orange and grey-brown, RHS 166D and 199A.

Foliage:

*Arrangement*.—Alternate.
*Attachment*.—Petiolate.
*Division*.—Simple.
*Shape*.—Palmate.
*Aspect*.—Nearly flat.
*Attitude*.—Outward.
*Length*.—58.0 mm.
*Width*.—52.0 mm.
*Apex*.—Obtuse.
*Base*.—Truncate.
*Margins*.—Dentate; ciliate.
*Texture and pubescence, adaxial surface*.—Bullate and glabrous except for the veins which are pubescent.
*Texture and pubescence, abaxial surface*.—Bullate and glabrous except for the veins which are pubescent.
*Luster, adaxial surface*.—Slightly glossy.
*Luster, abaxial surface*.—Slightly glossy.
*Color*.—Juvenile foliage color, adaxial surface — Yellow-green, nearest to RHS 144A. Juvenile foliage color, abaxial surface — Yellow-green, nearest to RHS 144B. Mature leaf color, adaxial surface — Green, nearest to RHS 137B. Mature leaf color, abaxial surface — Green, nearest to RHS 137C.
*Venation*.—Type — Reticulate. Vein color, adaxial surface — Yellow-green, nearest to RHS 144B. Vein color, abaxial surface — Yellow-green, nearest to a mixture of RHS 146A and 146B.
*Petiole*.—Length — 19.0 mm. Diameter — 3.0 mm. Strength — Strong. Texture, adaxial and abaxial surfaces — Pubescent. Luster, adaxial and abaxial surfaces — Matte. Color — Yellow-green, nearest to in between RHS 145A and 146D, and becoming progressively suffused with greyed-purple with age, RHS 183B.
*Stipules*.—General — Two stipules are present at the base of each leaf. Shape — Narrowly deltoid. Length — 8.0 mm. Width — 4.25 mm at the widest point. Aspect — Concave. Apex — Acute. Base — Truncate. Margin — Entire; no undulation. Texture, adaxial — Pubescent. Texture, abaxial — Pubescent. Luster — Matte on both the adaxial and abaxial surfaces. Color, adaxial surface — Yellow-green, nearest to RHS 145A, and margined greyed-purple, RHS 183D. Color, abaxial surface — Yellow-green, RHS 1456, and margined greyed- purple, RHS 183D.

Inflorescence: No inflorescences; flowers borne singularly or in pairs at leaf axils.

Flower buds:

*Shape*.—Obovoid, with a pointed apex; pentangulate.
*Length*.—22.0 mm.
*Diameter*.—16.0 mm.
*Texture*.—Pubescent.
*Luster*.—Slightly glossy.
*Color*.—Yellow-green, nearest to in between RHS 144B and 146D, and suffused with greyed-purple, RHS 183B, along the margins and apices of the closed sepals.

Flowers:

*Shape, type*.—Rotate, with a single whorl of petals; petals overlapping.
*Attachment*.—Pedicellate.
*Flowering habit*.—Freely flowering from late spring through Autumn in USDA Hardiness Zone 9.
*Attitude*.—Outward.
*Flower longevity on plant*.—Approximately 5 days.
*Persistent or self-cleaning*.—Self-cleaning.
*Fragrance*.—Non-fragrant.
*Diameter*.—Diameter of the corolla is 57.0 mm.
*Depth*.—Depth of the corolla is 26.0 mm.
*Pedicels*.—Length — 18.0 mm. Width — 3.5 mm at the base. Strength — Moderately strong. Texture —

Pubescent. Color — Yellow-green, nearest to a mixture of RHS 144B and 146D, and moderately suffused with greyed-purple at anthesis, nearest to RHS 183C.

*Calyx*.—Shape — Rotate. Depth — 18.0 mm. Diameter — 22.0 mm. Sepals — Quantity — 5. Shape — Deltoid. Dimensions — 17.0 mm long and 9.0 mm wide at the widest point. Apex — Acute. Base — Fused. Margin — Entire. Texture — Pubescent. Luster — Matte. Color —Yellow-green, nearest to a mixture of RHS 144A and 146D, and heavily suffused with greyed-purple at anthesis, nearest to RHS 183C.

*Episepals*.—Quantity — 3. Shape — Narrowly deltoid. Dimensions — 9.5 mm long and 3.0 mm wide at the base. Apex — Acute. Base — Fused. Margin — Entire. Texture — Pubescent. Luster — Matte. Color — Yellow-green, nearest to a mixture of RHS 144A and 146D, and heavily suffused with greyed-purple at anthesis, nearest to RHS 183C.

*Petals*.—Quantity — 5. Arrangement — Rotate. Length — 25.0 mm. Width — 28.0 mm. Shape — Near-obcordate. Aspect — Petals are somewhat reflexed at anthesis. Apex — Retuse. Base — Attenuate. Margin — Entire; very light undulation. Texture, inner surface — Glabrous; coriaceous. Texture, outer surface — Glabrous; coriaceous. Petal color — When opening, outer surface — Red-purple, nearest to a mixture of RHS 58C and 58D; base of the petal is red, nearest to RHS 53D. When opening, inner surface — Red-purple, nearest to a mixture of RHS 58C and 58D; base of the petal is red, nearest to RHS 53D. Fully opened, outer surface — Red, nearest to in between RHS 55D and 56D; base of the petal is red, nearest to RHS 53D. Fully opened, inner surface — Red, nearest to RHS 55D, and becoming lighter distally, nearest to RHS 56D; base of the petal is red, nearest to RHS 53D. Petal venation color — Pattern — Reticulate. Inner surface — Red, nearest to RHS 53D. Outer surface — Red, nearest to RHS 53D.

Reproductive organs:

*Staminal column*.—Description — A staminal column bears an abundance of stamens along its distal portion and terminates with a lobed pistil; the style is enveloped within the staminal column. Length — 12.0 mm, excluding the lobed stigma. Width —3.5 mm. Color — Red, nearest to RHS 53D.

*Androecium*.—Stamens — Quantity — Approximately 80. Anthers — Attachment — Dorsifixed. Shape — Globular. Dimensions — 1.0 mm long and 0.75 to 1.0 mm wide. Color — Black, RHS 202A. Filaments — Length — 8.0 mm. Diameter — 0.75 mm. Color — Red, nearest to a combination of RHS 55A and 55B. Amount of Pollen — Moderately abundant. Pollen color — Greyed-yellow, nearest to RHS 162C.

*Gynoecium*.—Pistil — Quantity — One. Length — 15.0 mm. Style — Not visible within the staminal column. Stigma — Shape — Lobed, with approximately 14 lobes. Length — 8.5 mm. Width — 11.0 mm across the stigma lobes. Color — Red-purple, RHS 57C. Ovary position — Superior.

Seed and fruit: Seeds not observed.

COMPARISONS WITH THE PARENT PLANTS

Plants of the new cultivar 'IB710-1' differ from the seed parent, *Anisodontea capensis* 'Dryspell Raspberry' (not patented), in the following characteristics described in Table 1 below.

TABLE 1

| Characteristic | 'IB710-1' | 'Dryspell Raspberry' |
|---|---|---|
| Growth habit. | More compact and densely foliaged. | Less compact and less densely foliage. |
| Foliage size. | Larger than 'Dryspell Raspberry'. | Smaller than 'IB710-1'. |
| Flower size. | Larger than 'Dryspell Raspberry'. | Smaller than 'IB710-1'. |
| General coloration of the corolla. | A relatively dark shade of red at the center of the corolla and becoming progressively lighter red towards the apex and margins. | Dark red-purple. |

Plants of the new cultivar 'IB710-1' differ from the pollen parent and most similar variety known to the inventor, *Anisodontea capensis* 'El Royo' (not patented), in the following characteristics described in Table 2 below.

TABLE 2

| Characteristic | 'IB710-1' | 'El Royo' |
|---|---|---|
| Growth habit. | More densely foliaged than 'El Royo' | Less densely foliaged than IB710-1'. |
| Plant height. | Shorter than the pollen 'El Royo'. | Taller than 'IB710-1'. |
| General coloration of the corolla. | A relatively dark shade of red at the center of the corolla and becoming progressively lighter red towards the apex and margins. | Red-purple at the center of the corolla, with a relatively lighter shade of red-purple elsewhere on the flower petals. |

Plants of the new cultivar 'IB609-3' differ from the most similar variety of common knowledge, *Anisodontea capensis* 'New Princess' (not patented), in the following characteristics described in Table 3 below.

TABLE 3

| Characteristic | 'IB710-1' | 'New Princess' |
|---|---|---|
| Plant height. | Shorter than 'New Princess. | Taller than 'IB710-1'. |
| Flower size. | Larger than 'New Princess'. | Smaller than 'IB710-1'. |
| General coloration of the flower petals. | A relatively dark shade of red at the center of the corolla and becoming progressively lighter red towards the apex and margins. | Red-purple, generally appearing as mauve pink. |
| General coloration of the floral veins. | Dark red. | Dark red-purple. |

That which is claimed is:

1. A new and distinct variety of *Anisodontea capensis* plant named 'IB710-1', substantially as described and illustrated herein.

* * * * *